United States Patent [19]

Benjamin et al.

[11] Patent Number: 5,491,068

[45] Date of Patent: Feb. 13, 1996

[54] ASSAY METHOD FOR DETECTING THE PRESENCE OF BACTERIA

[75] Inventors: Thomas L. Benjamin, Cambridge; Joan Chen-Wu; Thomsen Hansen, both of Brookline; Barbara Jackson, Roslindale; David Livingston, Brookline; Steven Tannenbaum, Framingham; Gerald Wogan, Belmont, all of Mass.

[73] Assignee: Vicam, L.P., Watertown, Mass.

[21] Appl. No.: 999,363

[22] Filed: Dec. 31, 1992

Related U.S. Application Data

[63] Continuation-in-part of Ser. No. 654,967, Feb. 14, 1991, abandoned.

[51] Int. Cl.⁶ .................. G01N 33/02; G01N 33/538; G01N 33/547; G01N 33/569

[52] U.S. Cl. .................. 435/7.32; 435/7.31; 435/7.33; 435/7.35; 435/7.37; 435/7.92; 435/7.95; 435/261

[58] Field of Search .................. 435/6, 7.31, 7.32, 435/7.33, 7.35, 7.37, 7.92, 7.95, 261

[56] References Cited

U.S. PATENT DOCUMENTS

| | | | |
|---|---|---|---|
| 3,970,518 | 7/1976 | Giaever | 436/526 |
| 4,230,685 | 10/1980 | Senyei et al. | |
| 4,677,055 | 6/1987 | Dodin et al. | 436/526 |
| 4,683,202 | 7/1987 | Mullis | 435/172.3 |
| 4,695,393 | 9/1987 | Whitehead et al. | 436/526 |
| 5,089,386 | 2/1992 | Stackebrandt et al. | 435/6 |

FOREIGN PATENT DOCUMENTS

| | | |
|---|---|---|
| 0498920 | of 0000 | European Pat. Off. |
| 89/06699 | 7/1989 | WIPO |
| 9008841 | 8/1990 | WIPO |
| 91/02811 | 3/1991 | WIPO |
| 92/08805 | 5/1992 | WIPO |
| 92/15883 | 9/1992 | WIPO |

OTHER PUBLICATIONS

Gustafsson et al, "Rapid Detection of Bordetella Pertussis by a Monoclonal Antibody–Based Colony Blot Assay", J. Clin. Microbiol., 27(4):628–631 (Apr. 1989).
FDA Bacterial Analytical Manual, 7th ed., Chapter 10, 1992.
Vermunt et al., J. Applied Bacteriology, 72, 112–118 (1992).
Johne et al., J. Clinical Microbiology, 27, 1631–1635 (1989).
Skjerve et al., Appl. Env. Microbiol. 56, 3478–3481 (1990).
Lund et al., J. Clinical Microbiology, 29, 2259–2262 (1991).
Forsgren et al., J. Immunology, 99, 19–24 (1967).
Weetall, Methods in Enzymology, 44, 134–148 (1976).
Hijmans et al., Clin. Exp. Immunol. 4, 457–472 (1969).
Goding, J. Immunological Methods, 13, 215–226 (1976).
Engvall, Methods in Enzymology, 70, 419–439 (1980).

*Primary Examiner*—Toni R. Scheiner
*Assistant Examiner*—Nancy J. Parsons
*Attorney, Agent, or Firm*—Birch, Stewart, Kolasch & Birch

[57] ABSTRACT

An assay method is provided to easily and quickly detect the presence of organisms capable of being cultured, such as bacteria, characterized by antibody capture of the organism of interest by use of specialized magnetic beads, incubation of the captured cells to form colonies; removal of material from the colonies with a colony lift membrane; and detection of the colony material on the membrane sheet by use of labeled antibodies, PCR or nucleic acid probes.

75 Claims, No Drawings

ASSAY METHOD FOR DETECTING THE PRESENCE OF BACTERIA

This application is a continuation-in-part of application Ser. No. 07/654,967 filed on Feb. 14, 1991, abandoned the entire contents of which are hereby incorporated by reference.

FIELD OF THE INVENTION

This invention relates to an assay method for quickly and easily detecting the presence of bacteria or other culturable organisms. In particular, an immunoassay method is utilized to detect the presence of viable bacteria in foods and other potentially contaminated samples using an assay characterized by 1) capture of specific bacterial cells with specific antibodies immobilized on magnetic beads; (2) incubation of the captured cells by the beads to form bacterial colonies; (3) imprint of the colonies to a colony lift membrane; and (4) confirmation and quantification of the colonies on the colony lift membrane.

BACKGROUND OF THE INVENTION

The presence of bacterial pathogens is a well recognized cause of severe illness, so that there is an ever present need for the detection of such pathogens in both clinical specimens (i.e. blood, tissue, urine and other body extracts and fluids), agricultural specimens (such as food products) and environmental specimens (such as surfaces in food processing plants).

However, current tests for the detection of bacterial pathogens, such as in food, typically require a number of days to complete. During this period of time, between sampling and assay determination, fresh food and dairy products will enter the food chain and therefore be consumed by the public. If a test indicates the presence of pathogens, expensive product recalls may result, or, worse, before the test results are discovered an outbreak of sickness may occur.

As stated above, traditional methods to detect the presence of bacterial food pathogens require an extended period of time, basically due to the need for an enrichment/incubation period. This incubation/enrichment period is intended to allow for growth of these bacteria from a background of competing microorganisms and an increase in bacterial cell numbers to more readily aid in identification. In many cases a series of two or three separate incubations is needed to isolate the target bacteria. However, such enrichment steps can actually compromise test sensitivity by killing some of the cells sought to be measured.

In the standard FDA procedure for detection of Listeria in food products (Bacteriological Analytical Manual, 7th Ed., 1992; Chapter 10) 25 g or 25 ml of a food sample is mixed with 225 ml of enrichment broth. This sample in broth mixture is incubated for 2 days. At the end of days 1 and 2 a sample of the broth culture is streaked onto petri plates containing selective growth agar and these plates are incubated for an additional 1–2 days. Identification of Listeria colonies is done by eye. This identification, however, is subjective, and presumed colonies must be confirmed by additional tests, which require another 1–2 days. Because of growth of bacteria during the enrichment step, the number of colonies on the agar plates does not represent the number of bacteria in the original sample. This test can only detect the presence of bacteria, and cannot quantitate the numbers originally present in the sample.

More recent methods of bacteria detection in food products have attempted to reduce the time needed for enrichment or confirmation. Many of these procedures utilize antibodies. A typical procedure, exemplified by the Listeria-Tek and Salmonella-Tek assays (Organon Technica Corp.), is a two site assay. That is, one antibody is immobilized in a microtiter well and acts to capture the target bacteria. This allows for separation of the target bacteria from the sample. A second antibody labelled with an enzyme is used to detect the captured bacteria. Theoretically, such an assay could be used to detect bacteria directly in a food sample. The actual sensitivity limit of these assays, however, makes it necessary to culture the target bacteria from the food sample. Because of the need for enrichment, the assay still requires 24–48 hours, even though the confirmation step is reduced to 1–2 hours. Enrichment also makes quantitation impossible.

Another alternative method for Listeria detection is immunomagnetic isolation. In this procedure, antibodies to the bacteria of interest are immobilized on magnetic beads. The beads, with attached antibodies, interact with the target organisms, which can be separated from other sample material and microorganisms in a magnetic field. This procedure is intended to reduce or eliminate the 24–48 hours enrichment period. Production and use of magnetic beads have been described in U.S. Pat. Nos. 3,970,518 (Giaever), 4,230,685 (Senyi and Widder), 4,677,055 (Dodin et al.), and 4,695,393 (Whitehead et al.). Immunomagnetic beads have been used to isolate Salmonella (Vermunt et al., J. Appl. Bact. 72, 112, 1992), *Staphylococcus aureus* (Johne et al., J. Clin. Microbiol. 27, 1631, 1989) and Listeria (Skjerve et al., Appl. Env. Microbiol. 56, 3478, 1990) from foods, and *Escherichia coli* from fecal samples (Lund et al., J. Clin. Microbiol. 29, 2259, 1991). In all of these examples, immunomagnetic capture is very inefficient at low numbers of bacteria. At the low levels of bacteria significant in food microbiology (<100 bacteria per gram), these methods cannot be used without enrichment. Interference by non-target organisms sometimes occurs, requiring the addition of selective enrichment, or a confirmation step, or both, to make a complete assay.

In summary, these existing "rapid" immunoassay procedures for bacteria detection in food samples all require at least one dilution of sample into growth medium, followed by an enrichment period, then an assay procedure which only utilizes a fraction of this final culture. The actual assay sample thus only corresponds to a small fraction of the original food sample. The bacterial culture step, or steps,, must therefore overcome this dilution factor, adding to the amount of needed culture time. The use of the enrichment step also makes quantification of bacteria impossible. In addition, the utilized enrichment steps may kill the bacteria sought to be identified, producing a high false negative rate.

The method of the present invention overcomes the low capture efficiency characteristic of all previous immunomagnetic procedures. Immunomagnetic capture of bacteria is a complex process, and several parameters are important in successful capture. Good recovery of bacteria from food samples requires strong interaction between the bacteria and the immunomagnetic beads. The higher efficiency of the assay of the present invention results from improvements in both particle design and the method used for magnetic isolation.

A combination of bead porosity, bead size, attachment method, and long capture time accounts for the improved performance. The improvement in capture efficiency is such that bacteria can be isolated directly from food samples, without enrichment, at levels of less than 10 bacteria per gram of food. Because enrichment is avoided, the method allows quantitation of the number of bacteria present. In addition, the bacterial colonies formed are individually confirmed as target bacteria by an immunochemical confirmation step.

OBJECTS AND SUMMARY OF THE INVENTION

It is, therefore, an object of the present invention to provide a method for the detection of viable bacteria which eliminates the selective culturing steps.

It is another object of the invention to provide a method for quickly confirming and quantitating the presence of any culturable organism, particularly bacteria, including potentially pathogenic bacteria.

It is a further object of the invention to provide a method for the detection of bacteria by which the detection can be easily made by viewing with the human eye.

These and other objects of the invention are accomplished by providing a method wherein:

(1) the bacteria cells of interest are selectively captured and removed from a sample by the use of an antibody bound to magnetic beads;

(2) the captured bacteria cells are spread on a medium to form colonies;

(3) the bacteria colonies are contacted with a colony lift membrane to attach colony material to the membrane; and (4) the presence of colony material from the colonies of the bacteria of interest is detected by use of one of various procedures, including DNA or RNA probes, PCR techniques and labeled antibodies which provide evidence of the presence of the bacteria of interest.

DETAILED DESCRIPTION OF THE INVENTION

As noted above, one object of the invention is to provide an assay procedure for rapid and easy identification of the presence of a particular bacteria of interest in a sample. The assay procedure is broadly applicable to the detection of any culturable organism, including bacteria, molds and yeast. Of particular importance is the detection of the presence of potentially harmful contaminants, particularly those which cannot be visually detected by eye. A broad range of contaminants can be detected by the assay, so long as the contaminant can be cultured to form colonies and antibodies can be raised against the contaminant, DNA or RNA probes can be used to detect the contaminant or PCR techniques can be used to detect DNA material from the contaminant.

In a particular preferred aspect, the assay is used to detect various bacteria, and can be utilized to detect the presence of any specific, selected bacteria of interest. The bacteria can be either pathogenic or non-pathogenic, although the invention is particularly important for detection of potentially contaminating pathogenic bacteria. Specific bacteria detectable by the assay of the invention include, for example, Listeria, Campylobacter, *Escherichia coli*, Salmonella, Clostridia (such as *Clostridium botulinum* and *Clostridium perfingens*), Shigella, Staphylococci (such as *Stapylococcus aureus*), Vibrio (such as *Vibrio vulnificus, Vibrio cholerae* and *Vibrio parahaemolyticus*), Yersinia (such as *Yersinia enterocolitica* and *Yersinia pseudotuberculosis*) Plesiomonas strigelloides, Bacilli (such as *Bacillus cereus*) and Aeromonas (such as *Aeromonas hydrophila*).

In addition, various molds can be detected, including Byssochlamys, Fusarium, Geotrichum, Penicillium and Scopulariopsis and various yeasts can be detected, such as Kluyveromyces, Pichia, Saccharomyces, Candida and Rhodotorula.

The method of the invention, therefore, ,generally comprises the following procedural steps:

1) The sample to be tested is, if necessary, liquified or otherwise prepared for use in the assay.

2) The liquid sample is combined with magnetic beads having immobilized thereon monoclonal or polyclonal antibodies to the selected bacteria of interest, the presence of which is to be determined by the assay. If present, the target selected bacteria cells are thereby immobilized onto the immunomagnetic beads. The immunomagnetic beads with attached immobilized bacteria are then washed to remove any remaining sample.

3) The immunomagnetic beads with the immobilized bacteria are then spread on a culture medium, and the bacteria are allowed to grow to form colonies.

4) To confirm that the colonies are the bacteria of interest, the colonies are then contacted with a colony lift membrane, and the membrane is removed, whereby the colony material from the bacterial colonies is attached to the lift membrane.

5) The colony material attached to the lift membrane is then subjected to one of several detection/analytical procedures by which the presence of the bacteria of interest can be either qualitatively or quantitatively determined. These detection steps include: (a) use of nucleic acid probes; (b) use of PCR; and (c) use of antibodies.

(a) If nucleic acid probes are used, the lift membrane (nitrocellulose) is placed in a lysis buffer to allow lysis of the bacterial colonies and release bacterial nucleic acids which become bound to the lift membrane. The membrane is then blocked and hybridization is carried out directly in the blocking solution by adding to it a RNA or DNA probe specific for the bacteria of interest. The probe is, for example, labeled with fluorescein, so that, the hybridized membrane can then be incubated with an anti-fluorescein antibody labelled for subsequent detection.

(b) If PCR detection is to be used, again the lift membrane having colony material attached thereto is added to a lysis buffer to release nucleic acids. The released nucleic acids are then precipitated, collected and form the template for a PCR reaction. The template nucleic acid is appropriately mixed with nucleoside triphosphates, divalent cations and primers.

(c) If antibody detection is to be used, the lift membrane is treated with a fixing agent to fix the colony material to the membrane and the membrane is blocked to lower nonspecific reactivity. The membrane, having fixed thereto material from the bacterial colonies, is then treated with a labeled or unlabeled first antibody specific to the bacteria of interest to be detected, and the membrane is washed to remove any unbound first antibody. If the first antibody was unlabeled, the membrane is then treated with a second antibody which is labeled and specific for the first antibody, and the membrane is washed to remove any unbound labeled second antibody. The presence of labeled first or second antibody on the membrane is then detected, specifically by means to permit visual evidence of the presence of colonies of the bacteria of interest.

As can be seen from the above method scheme, the method of the invention is particularly characterized by the use of immunomagnetic beads to first select out bacteria from a sample. The beads must be capable of efficiently capturing bacteria from foods at realistic levels, while not capturing other bacteria which may be present at much greater numbers. The antibody used for this step need not be totally specific to the bacteria of interest as subsequent selective and specific steps combine to confer the ultimate specificity of the assay for only specific bacteria of interest. Further uniquely characterizing the method of the invention is the use of a colony lift membrane and subsequent confirmation steps. Using these characteristic features, the method of the invention can be importantly applied to the rapid and specific detection of viable strains of bacteria, particularly detection by a simple visual means, detectable by the human eye. The assay particularly provides a very sensitive assay detection, capable of detecting 1 colony forming unit (CFU) per 25 ml of sample, more than 100 times more sensitive than prior immunomagnetic methods.

High sensitivity and efficiency of the assay of the invention are accomplished by an important combination of factors relating to the design and use of magnetic beads having antibodies attached thereto.

First, the antibodies must be accessible at the surface of the magnetic beads, so nonporous beads are required. Giaever, Senyi, and Dodin (cited above) all disclose the use of porous magnetic beads. Second, the antibodies must be oriented with their binding sites outward. In one embodiment, attachment of antibodies to magnetic particles is accomplished through a protein A intermediate. That is, protein A is first attached to the magnetic particles and the antibodies of choice are then bound to the protein A. The use of the protein A intermediate greatly increases the effectiveness of capture by the attached antibodies (Forsgren et al., J. Immunol. 99, 19, 1967). Protein A attaches to the Fc portion of IgG subclass antibodies, thus extending and presenting the Fab portion of these antibodies. The resulting correct orientation of the antibodies and extension away from the particles leads to a very effective interaction between the bound antibodies and their target. Senyi describes protein A magnetic beads, but without the other improvements described here, those would not be successful. Third, the magnetic particles must be in the submicron size range, which creates a large surface area. Skjerve used solid polystyrene beads of 2.8 μm diameter, and these were much less efficient. Fourth, contact time between the beads and the bacteria must be long enough to allow strong interaction. Magnetic beads are mixed with sample for 30 minutes to 2 hours, a longer time than reported in previous trials of magnetic beads.

Step 1: Liquefaction

The assay of the invention can be utilized to detect the presence of bacteria in a wide variety of samples, both solid and liquid, including food, agricultural products, environmental samples and various clinical specimens. If the sample is liquid, it can be per se subjected to the procedure of the invention, or first diluted, or concentrated centrifugation. On the other hand, if the sample is solid, it should be first liquified (for example in water) using standard known techniques, such as by use of a blender or stomacher. The liquid or liquified sample may, if desired, be filtered through a course paper, glass or other matrix filter to remove particulates. If the sample to be tested is environmental sample, then swabs or scrapings of the tested surface or material are mixed in a collection buffer and then treated as a liquified food sample.

Step 2: Immobilization With Antibodies

Antibodies (polyclonal or monoclonal) to target bacterial cells are immobilized on magnetic beads and used to separate the bacteria cells from the sample. In this step, one or more antibodies may be used to recognize all target strains of the bacteria genus of interest. The antibodies used in this step recognize bacteria cell surface antigens. After an incubation period in which the liquid sample or liquified sample is mixed with the magnetic particles having antibodies attached, the antibody bound particles and attached bacteria are then separated from the sample by means of a magnetic field (magnetic capture) and washed to remove other potential impurities.

As the antibodies for capture, and, as discussed later, for detection, of the bacteria, any class of antibodies can be used (including IgG and IgM) and either polyclonal antibodies or monoclonal antibodies can be used depending upon various factors, including the degree of sensitivity desired. If polyclonal antibodies are to be used, then such antibodies can be prepared according to per se known procedures. For example, procedures such as those described by Hurn, B. A. et al. (1980) in Metho in Enzymology, Ed. Van Vanakis, H. and Langone, J., pp. 104–142, can be used. The preparation of monoclonal antibodies is known and if monoclonal antibodies are to be used in this invention, they are prepared using the method originally authored by Milstein and Kohler and published in Nature (1975), 256, pps. 495–497.

The magnetic beads must meet several requirements in order to be useful in this assay. They must be nonporous, so that the antibody molecules remain on the surface of the bead, where they an contact the bacteria. The magnetic beads described in U.S. Pat. Nos. 3,970,518 (Giaever), 4,230,685 (Senyi and Widder), and 4,677,055 (Dodin et al.) are all porous, allowing antibody molecules to enter the beads. Since the bacteria cannot enter the bead, the amount of antibody available to contact bacteria is reduced. In addition, the beads must be less than about 1 μm in diameter, so that the beads are similar in size as, or smaller than, the bacteria. The magnetic beads used by Skjerve (cited above), commercially available from Dynal, were 2.8 μm. Their low capture efficiency was due in part to the relatively large bead diameter.

Beads for use in the present invention, therefore, are non-porous and have a diameter of from about 50 nm to about 1 μm, preferably from 0.3 to 1 μm. The beads must also contain a chemically functional group through which the antibody can be attached. The beads described by Whitehead et al. (U.S. Pat. No. 4,695,393) are suitable. Whitehead, however, does not describe capture of bacteria, and gives no indication that their beads would be an improvement over the larger or porous beads described earlier. Other suitable beads include protein coated magnetite beads, such as beads coated with bovine serum albumin which may be additionally coated with an antibody-linking compound like Protein A. Useful beads are described, for example in PCT Patent Publication WO 9102811 to Immunicon Corp. and are commercially available as Immunicon Protein A Magnetic Separation Media, Cat. No. G6100.

Attachment of the antibody to the magnetic beads must be such that the binding portion of the antibody extends away from the surface of the bead, allowing contact between the binding portion of the antibody and the bacteria. To do this, the antibody is attached at some site on its nonbiding portion. Potential sites for direct covalent biding include the carbohydrate portion and sulfhydryl groups between the heavy chains. The antibody can also be attached indirectly using a ligand or protein with affinity for the nonbinding portion, such as another antibody or protein A. Binding via protein A is a preferred method of this invention. The method of attachment of protein A to magnetic particles may proceed by any of several processes available through the scientific literature. In one such procedure, magnetic iron oxide particles of approximately 1 μm diameter, derivatized with an amino group, are chemically activated with glutaraldehyde. The activated magnetic particles are then mixed with protein A resulting in a magnetic particle to which protein A is covalently attached. The antibodies are then added to the protein A magnetic particles and after a short incubation the protein A-antibody complexes form (Weetall, Meth. Enzymol. 44, 134, 1976). These derivatized particles with protein A-antibodies attached are now ready for use in bacterial cell capture.

During the capture step, strong interactions must form between the antibodies and the bacteria.. A short incubation time, such as 5 minutes, allows only weak interactions to form, producing low capture efficiency. At least 30 minutes, and preferably 2 hours, is needed to allow sufficiently strong interactions to produce high capture efficiency.

Step 3: Growth of Bacterial Colonies

The captured and immobilized bacterial cells are spread on a medium on which the cells will grow and are incubated. Incubation is conducted for a time sufficient to form bacterial colonies visible to the eye. Spreading the cells produces separate colonies from the individual cells, providing a means of quantification.

Particular media for incubation depend, of course, upon the bacteria of interest to be detected. Such mediums, preferably solid, are per se known to those skilled in the art for various bacteria, as disclosed, for example, in the Bacteriological Analytical Manual. Incubation times and conditions are also varied and per se known, depending upon the particular bacteria of interest. Generally, sufficient growth is accomplished within 6 to 24 hours.

Alternatively, the separated bacteria can be grown in a liquid culture medium. This removes the possibility of quantitation, but still allows subsequent confirmation of the presence of the selected bacteria. Confirmation in this case can be by traditional biochemical tests, or by immunochemical or nucleic acid probe techniques.

Step 4: Colony Lift onto Membranes

After incubation of the bacteria is completed, confirmation of the specific bacteria of interest is still necessary. This can be done in various ways. For example, colonies can be confirmed by traditional biochemical methods or by one of the newer immunochemical or nucleic acid probe tests. The preferred form of this invention uses immunochemical confirmation on a colony lift membrane, in order to preserve the quantitative capabilities provided by the efficient magnetic capture step.

A colony lift membrane is placed in contact with the growth medium, whereby the colonies attach and imprint colony material to the membrane. Colony lift membranes are per se known and may be comprised of, for example, nitrocellulose or nylon. The membrane is preferably cut to the size of the container or dish containing the growth medium, so that all colonies growing on the container are overlayed with the same single sheet. In this manner, the sheet/membrane acquires the same pattern of colonies that was originally contained on the growth medium.

Step 5: Detection of Bacteria of Interest

The lift membrane having colony material can now be subjected to one of several procedures for detection of the bacteria of interest.

a) Detection by use of nucleic acid probes:

Detection of the bacteria of interest can be performed by use of nucleic acid probes following procedures which are per se known. Suitable procedures for such detection of Listeria are described, for example, in U.S. Pat. No. 5,089,386, PCT Patent Publ. WO 90/08841, PCT Patent Pub. WO 92/15883, and PCT Patent Pub. WO 89/06699, each of which is hereby incorporated by reference.

A suitable nucleic acid probe assay is comprised generally of (1) sample treatment and lysis; (2) hybridization with the selected probe(s); (3) hybrid capture and (4) detection.

Lysis of the bacteria is necessary to release the target molecules for the probes. The nucleic acid target molecules are released by treatment with any of a number of lysis agents, including alkali (such as NaOH), guanidine salts (such as guanidine thiocyanate), enzymes (such as lysozyme, mutanolysin and proteinass K), and detergents.

Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), however, is preferred because rNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization is comprised of the addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/reaction conditions is defined by the length and base composition of the probe/target duplex, as well as by the level and geometry of mispairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique rRNA sequences of the target organism. Suitable probes useful for the detection of Listeria are described, for example, in U.S. Pat. No. 5,089,386, PCT Patent Pub. WO 90/08841 and PCT Patent Pub. WO 89/06699 and are commercially available, for example, from Gene-Trak Systems. In general, a first capture probe is utilized to "capture" formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

b) Detection by use of PCR:

Detection of the bacteria of interest can also be performed by use of PCR techniques. A suitable PCR technique is described, for example, in PCT Patent Pub. WO 92/08805. Such detection procedures are applied to the colony material adhered to the lift membrane or, alternatively, directly to the bacteria captured on the magnetic beads. In either case, the bacteria is combined with a lysis buffer and collected nucleic acid target molecules are then utilized as the template for the PCR reaction.

c) Detection by use of antibodies:

For detection of the selected bacteria by use of antibodies, after the colony material is adhered to the lift membrane, it is then necessary to fix the colony material to the lift membrane by treatment with an appropriate fixing agent in order to ensure that the colonies adhere more firmly to the sheet. Suitable fixing treatments include placing the lift membrane in a solution of methanol or placing the membrane in a solution of the detergent sodium dodecyl sulfate with brief heating to 70° C.

It may also be desirable to treat the fixed colonies and membrane with per se known blocking agents to prevent non-specific reactivity of the subsequent detecting antibodies. Suitable blocking agents include, for example, casein and BSA.

The lift membrane having fixed thereto the colony material from the bacterial colonies is next contacted with antibodies specific to the bacteria of interest. As noted above, either polyclonal or monoclonal antibodies can be utilized, but in either case have affinity for the particular bacteria to be detected. These antibodies, when contacted with the lift membrane, will adhere/bind to material from the specific target bacteria colonies, but will not bind to the other colonies.

Useful polyclonal antibodies include, for example, those from Difo poly sera raised in rabbits. These antibodies can also be specific for particular strains to be detected. For example, Listeria monocytogenes includes strains of serovars 1/2a, 1/2b, 1/2c, 3a, 3b, 3c, 4a, 4a/b, 4b, 4c, 4d, 4e, 7, with strains of serovars 1/2a, 1/2b and 4b being the most common pathogenic strains. It is useful, therefore, to detect the presence in a sample of pathogenic Listeria by utilizing a polyclonal sera against Listeria serovars 1/2 and 4b. Other useful antibodies, polyclonal or monoclonal, are those specific for proteins or carbohydrates on the cell surface of the bacteria of interest. Of particular usefulness are monoclonal antibodies against Listeria teichoic acids of serovars 1/2 and 4b.

Treatment as described above with a first antibody, specific to the bacteria cells of interest, provides the first step for selection and identification of the specific bacteria of interest. The membrane sheet is then contacted with a second antibody. Again, this antibody may be either polyclonal or monoclonal, but importantly is (a) capable of binding to the first antibody and (b) labeled in a manner to enable subsequent detection.

If the first antibody is, for example, the above-noted Difco poly sera, then the second antibody is an anti-rabbit IgG/label conjugate. If the first antibody is a monoclonal antibody derived from mouse, than the second antibody is an anti-mouse IgG/label conjugate.

Alternatively, the first antibody (or the first capture nucleic acid probe described above) can itself be labelled. The assay can then proceed to detection of the label without the need for use of a second antibody (or a second detector probe).

With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goring, J. W. (1976), J. Immunol. Meth. 13,215-, for tetramethylrhodamine isothiocyanate, and the method of Engrall, E. (1980), Meth. in Enzymol. 70, 419–439 for enzymes.

These detector antibodies may also be labeled indirectly. In this case the actual detection molecule is attached to a secondary antibody or other molecule with binding affinity for the anti-bacteria cell surface antibody. If a secondary antibody is used it is preferably a general antibody to a class of antibody (IgG and IgM) from the animal species used to raise the anti-bacteria cell surface antibodies.

For example, the second antibody may be conjugated to an enzyme, either alkaline phosphatase or to peroxidase. To detect the label, after the membrane sheet is contacted with the second antibody and washed, the membrane sheet is immersed in a solution containing a chromogenic substrate for either alkaline phosphatase or peroxidase. A chromogenic substrate is a compound which can be cleaved by an enzyme to result in the production of some type of detectable signal which only appears when the substrate is cleaved from the base molecule. The chromogenic substrate is colorless, until it reacts with the enzyme, at which time an intensely colored product is made. Thus, material from the bacteria colonies adhered to the membrane sheet will become an intense blue/purple/black color, or brown/red while material from other colonies will remain colorless. Examples of detection molecules include fluorescent substances, such as 4-methylumbelliferyl phosphate, and chromogenic substances, such as 4-nitrophenylphosphate, 3,3', 5,5'-tetramethylbenzidine and 2,2'-azino-di-[3-ethelbenzthiazoliane sulfonate (6)]. In addition to alkaline phosphatase and peroxidase, other useful enzymes include β-galactosidase, β-glucuronidase, α-glucosidase, β-glucosidase, α-mannosidase, galactose oxidase, glucose oxidase and hexokinase.

Example 1—Detection of Listeria Utilizing Antibody Detection

The following is a specific example to show the use of the assay of the invention to particularly detect the presence of Listeria.

1. To magnetic particles approximately 0.3 μm in size with covalently attached protein A (such as Immunicon Protein A beads), add antibodies to Listeria (such as Lee Labs, Inc. Listeria O antiserum Poly 1,4).

2. Obtain sausage sample known by conventional microbiological methods to contain 100,000 to 1 million bacteria per gram and which contain 23 Listeria per gram, as determined by the FDA Most Probable Number Assay (MPN), and 2.3 Listeria per gram, as extrapolated from the FDA MPN assay. The MPN assay is accurate within one order of magnitude. The immunomagnetic capture procedure recovers 30% of Listeria from sausage samples.

3. Liquify the above samples as follows: add 25 grams sausage to 150 mL phosphate buffered saline (PBS)+0.05% Tween20, and stomach for two minutes at normal speed.

4. Filter the stomachate so that 40 mL filtrate is collected.

5. Centrifuge the 40mL filtrate at 11,000×g for 15 minutes to concentrate the microorganisms. Decant the supernatant and resuspend the pellet in 2 mL PBS+Tween.

6. Combine the 2mL resuspension, equivalent to 5.7 grams of the original sausage sample, with 100 μL of the magnetic beads having immobilized thereon antibodies to Listeria.

7. After an incubation time of 2 hours rotating end to end, place the mixture in a magnetic field to remove the magnetic beads having Listeria cells immobilized thereon, and wash the beads a total of two times with PBS to remove undesirable impurities and unbound material or cells.

8. Spread the separated magnetic beads on the surface of a petri dish containing brain-heart infusion agar, plus lithium chloride and ceftazidime.

9. After an incubation of 20 hours at 37° C., examine the plates for growth of bacterial colonies. In this example, duplicate plates from the 23 Listeria CFU/g per gram sausage sample contained 29 and 26 Listeria-like colonies, as well as several non-Listeria-like colonies. Plates from the 2.3 Listeria per gram sausage sample contained 8 and 2 Listeria-like colonies.

10. To confirm these suspected colonies as Listeria, place a colony lift membrane (e.g. Pall Biodyne Transfer Membranes) onto the plate of solid growth medium to obtain an imprint of the colonies on the membrane. Wait 5 minutes before peeling the membrane from the plate. The media plates may then be further incubated or stored at 4° C. for use in further testing.

11. Place the colony lift membrane, colony side up, into a tray containing 10 mL methanol for 5 minutes to kill bacteria and to fix antigens onto the membrane surface so that they will not wash off.

12. Wash the membrane under a fast flowing water tap to remove any excess colony material.

13. Wash the membrane with PBS+Tween for 2–5 minutes. Remove wash fluid and repeat wash two more times, for a total of three washes.

14. Block the membrane to prevent nonspecific reactivity of the detecting antibodies by placing the membrane in 10 mL PBS + Tween+2% nonfat dry milk. Shake on a reciprocating shaker for 30 minutes.

15. After the 30 minute incubation, pour off any remaining solution and wash the membrane a total of three times with PBS+Tween.

16. Incubate the membranes with 10mL of first antibody in PBS+Tween while shaking for 30 minutes. The antibody for this example is a mouse monoclonal IgM capable of binding to Listeria cell surface protein antigens fixed to the membrane.

17. After the 30 minute incubation, pour off the first antibody solution and wash the membrane a total of three times with PBS+Tween.

18. Incubate the membrane with 10 mL of second antibody (goat anti-mouse IgM antibody conjugated to alkaline phosphatase) diluted in PBS+Tween, while shaking for 30 minutes. The second antibody is capable of binding to the first antibody, which is specific to Listeria, so that color is produced on the membrane at places where antigens from the Listeria colonies are present.

19. Pour off the second antibody solution and wash the membranes with 10 mL water, for a total of three washes.

20. Incubate the membranes with 10 mL of alkaline phosphatate substrate solution on the shaker until purple dots appear on the membrane. A typical incubation requires about 5 minutes.

21. Stop the reaction by pouring off the substrate and washing with 10 mL water per membrane, for a total of two washes.

22. The number of Listeria is then quantitated by counting the number of purple signals formed on each membrane. In this example the 23 CFU/g samples' membranes contained 29 and 26 purple signals, while the 2.3 CFU/g samples' membranes contains 8 and 2 purple signals corresponding to the Listeria-like colonies on the media plates, thus confirming that they are Listeria. No purple signals were present at the positions corresponding to the non-Listeria-like colonies.

23. The original contamination level determined by Listertest is calculated. The sausage samples containing 23 CFU/g, as determined by MPN, contained 16 CFU/g as determined by this method. The sausage samples containing 2.3 CFU/g, as determined by MPN, contained 2.9 CFU/g as determined by this method.

Example 2—Listeria Detection Utilizing Nucleic Acid Probe Detection

Selective capture of Listeria is performed the same as in Example 1 up to the stage at which the colony lift membrane is used to obtain an imprint of the colonies (step 10). For this procedure a lift membrane is comprised of nitrocellulose (NC). The NC membrane is laid over colonies on the master plate for five minutes to make an imprint. The imprinted membrane is then placed in a lysis buffer (1% (w/v) sodium dodecyl sulfate in water) at 37° C. for 30 minutes, to allow lysis of bacterial colonies and the release of bacterial nucleic acids, which become bound to the NC membrane. This step is followed by a gentle wash in room temperature buffer, followed by fixing of the DNA onto the NC membrane by heating the dry membrane at 70° C. for 2 hours. The NC membrane is then blocked with 0.1% (w/v) bovine serum albumin in wash buffer. Hybridization is carried out directly in the blocking solution by adding to it a DNA probe specific for Listeria species or Listeria monocytogenes and labeled with fluorescein. Hybridization is carried out at 37° C. for one hour.

The NC membrane is then washed at 37° C. for five minutes, and at 65° C. for five minutes, using the wash buffer. The NC membrane is then incubated with an antifluorescein antibody labelled with alkaline phosphatase. Alternatively the probe is a biotinylated DNA probe and detection is by use of avidin-labelled enzyme. The NC membrane is incubated with substrate, bromo-chloro-indoyl-phosphate and nitro-blue-tetrazolium, until blue dots appear over colony material or the background becomes pale blue. If Listeria are present, there is color formation on the membrane corresponding to colonies of Listeria on the master plate.

Example 3—Listeria Detection Utilizing PCR

As noted above, PCR detection can be applied to either the bacteria as captured on the magnetic beads or to the bacteria colony material adhered to the lift membrane. In either case, the bacteria, either on the beads or from a colony, are mixed with a lysis buffer.

The lysis buffer contains the enzymes lysozyme and mutanolysin. These enzymes digest bacterial cell walls so the nucleic acids can be released. The sample in lysis buffer is incubated at 37° C. for 30 minutes. Then a small amount of lysis buffer containing proteinase K and detergent is added. Proteinase K digests protein. After a brief incubation, sodium acetate and absolute ethanol are added, to precipitate nucleic acid. The precipitated nucleic acid is centrifuged to collect it, and dried. This material forms the template in the PCR reaction.

The PCR reaction is begun by mixing template nucleic acid with nucleoside triphosphates and divalent cation, along with primer. Many sequences have been published for Listeria primers in PCR, any of which is suitable. TAC polymerase, a genetically engineered form of DNA polymerase, is added to the mixture and the solution is covered with mineral oil to prevent evaporation. The mixture is subjected to 30 cycles of PCR, followed by electrophoresis. DNA can be visualized by ethidium bromide or another type of visualization method. One picogram of template DNA is sufficient to produce detectable levels of amplified product under these conditions.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for detecting the presence of an organism capable of being cultured which comprises:
   a) combining a sample to be tested for the presence of a selected organism with a magnetic solid support having immobilized thereon antibodies to said selected organism, to thereby capture cells of said selected organism from said sample, said magnetic solid support being non-porous magnetic beads having a diameter of from 50 nm to 1 μm;

b) exposing to a magnetic field said magnetic beads having bound thereto said first antibodies and captured selected organisms to thereby separate said magnetic solid support from said sample;

c) culturing the thus captured magnetic solid support and captured selected organisms on a solid medium to form colonies of said selected organism;

d) contacting said colonies with a colony lift membrane whereby some colony material adheres to said membrane; and e) treating said membrane to detect the presence on said membrane of material from said colonies of said selected organism.

2. The method according to claim 1, wherein the antibodies to said selected organism are bound to said magnetic solid support through protein A.

3. The method according to claim 1, wherein said colony lift membrane is comprised of nitrocellulose or nylon.

4. The method according to claim 1, wherein after contacting with said colonies, said membrane is treated with a fixing agent to fix said colonies to said membrane.

5. The method according to claim 1, wherein said membrane with colony material adhered thereto is contacted with labelled detector antibodies which bind to said colony material of said selected organism and the presence of said detector antibody on said membrane is detected to provide evidence of the presence on said membrane of colony material from said selected organism.

6. The method according to claim 5, wherein said label is selected from the group consisting of fluorogenic, radioactive, chemiluminescent, bioluminescent, and enzyme substrate molecules.

7. The method according to claim 1, wherein said selected organism is a bacteria, yeast or mold.

8. The method according to claim 7, wherein said bacteria is a member selected from the group consisting of Listeria, Campylobacter, Escherichia, Salmonella, Clostridia, Shigella, Staphylococci, Vibrio, Yersinia, Plesiomonas, Bacilli and Aeromonas; said yeast is a member selected from the group consisting of Kluyveromyces, Pichia, Saccharomyces, Candida and Rhodotorula and said mold is a member selected from the consisting of Byssochlamys, Fusarium, Geotrichum, Penicillium and Scopulariopsis.

9. The method according to claim 8, wherein said bacteria is Listeria.

10. The method according to claim 9, wherein said bacteria is pathogenic strains of Listeria.

11. The method according to claim 1, wherein said lift membrane having colony material adhered thereto is combined with a lysis buffer to lyse organisms and release nucleic acids from said selected organism, said released nucleic acids are combined with and hybridized to a nucleic acid probe specific for said selected organism, and formation of a hybrid molecule is detected.

12. The method according to claim 1, wherein said lift membrane having colony material adhered thereto is combined with a lysis buffer to lyse organisms and release nucleic acids from said selected organisms, and said released nucleic acids are subjected to PCR to detect the presence of nucleic acid unique to said selected organism.

13. A method for detecting the presence of bacteria which comprises:

a) combining a sample to be tested for the presence of a selected bacteria with a magnetic solid support having immobilized thereon first antibodies to said selected bacteria, to thereby capture cells of said selected bacteria from said sample, said antibodies being attached to said solid support through a protein A intermediate such that the Fab portions of said antibodies extend outward from the surface of said solid support, said magnetic solid support being nonporous magnetic beads having a diameter of from 50 nm to 1 μm;

b) exposing to a magnetic field said solid support having bound thereto said first antibodies and captured bacteria cells to thereby separate said magnetic solid support from said sample;

c) culturing said magnetic solid support and captured bacteria cells on a solid medium to form colonies of said bacteria;

d) contacting said colonies with a colony lift membrane whereby colony material from said colonies adheres to said membrane;

e) contacting said membrane and said colony material adhered thereto with second antibodies specific for said selected bacteria, whereby said second antibodies bind to said colony material from said colonies of said selected bacteria;

f) contacting said membrane with labeled antibodies specific for said second antibodies, whereby said labeled antibodies bind to said second antibodies bound to said colonies of said selected bacteria; and g) treating said membrane to provide evidence of the presence on said membrane of the label on said labeled antibody and colonies of said selected bacteria.

14. The method according to claim 13, wherein said colony lift membrane is comprised of nitrocellulose or nylon.

15. The method according to claim 13, wherein after contacting with said bacteria colonies, said membrane is treated with a fixing agent to fix said colonies to said membrane.

16. The method according to claim 13, wherein said label is selected from the group consisting of fluorogenic, radioactive, chemiluminescent, bioluminescent, and enzyme substrate molecules.

17. The method according to claim 13, wherein said selected bacteria is a member selected from the group consisting of Listeria, Campylobacter, Escherichia, Salmonella, Clostridia, Shigella, Staphylococci, Vibrio, Yersinia, Plesiomonas, Bacilli and Aeromonas.

18. The method according to claim 17, wherein said selected bacteria is Listeria.

19. The method according to claim 13, wherein said first antibodies are polyclonal antibodies to said selected bacteria.

20. The method according to claim 19, wherein said second antibodies and labeled antibodies are monoclonal antibodies.

21. The method according to claim 13, wherein said labeled antibody is labeled with an enzymatic molecule, which when treated, produces a color change to provide visual evidence of the presence on said membrane of said label and colonies of said selected bacteria.

22. The method according to claim 21, wherein said enzymatic molecule is peroxidase, alkaline phosphatase, β-galactosidase, β-glucuronidase, α-glucosidase, β-glucosidase, α-mannosidase, galactose oxidase, glucose oxidase, or hexokinase.

23. The method according to claim 22, wherein said membrane is treated with a chromogenic substance for said enzymatic molecule.

24. A method for determining the quantity of Listeria in a sample which comprises:
   a) combining a sample to be tested for the presence of Listeria with a magnetic solid support having immobilized thereon antibodies to said Listeria, to thereby capture cells of said Listeria from said sample, said magnetic solid support being non-porous magnetic beads having a diameter of from 50 nm to 1 μm;
   b) exposing to a magnetic field said magnetic beads having bound thereto said first antibodies and captured Listeria cells to thereby separate said magnetic solid support from said sample;
   c) culturing the thus captured magnetic solid support and captured Listeria on a solid medium to form colonies of said Listeria;
   d) contacting said colonies with a colony lift membrane whereby some colony material adheres to said membrane; and
   e) treating said membrane to detect the presence on said membrane of material from said colonies of said Listeria and to provide a quantification of the amount of Listeria in said sample.

25. The method according to claim 24, wherein the antibodies to said Listeria are bound to said magnetic solid support through protein A.

26. The method according to claim 24, wherein said colony lift membrane is comprised of nitrocellulose or nylon.

27. The method according to claim 24, wherein after contacting with said colonies, said membrane is treated with a fixing agent to fix said colonies to said membrane.

28. The method according to claim 24, wherein said membrane with colony material adhered thereto is contacted with detector antibodies conjugated with a label which bind to said colony material of said Listeria to provide evidence of the presence on said membrane of colony material from said Listeria and the number of colonies having labeled detector antibodies bound thereto is counted to provide a quantitative measure of the number of Listeria in said sample.

29. The method according to claim 28, wherein said label is selected from the group consisting of fluorogenic, radioactive, chemiluminescent, bioluminescent, and enzyme substrate molecules.

30. The method according to claim 9, wherein said lift membrane having colony material adhered thereto is combined with a lysis buffer to lyse bacteria and release nucleic acids from said Listeria, said released nucleic acids are combined with and hybridized to a nucleic acid probe specific for said Listeria, and formation of a hybrid molecule is detected.

31. The method according to claim 9, wherein said lift membrane having colony material adhered thereto is combined with a lysis buffer to lyse Listeria and release nucleic acids from said Listeria, and said released nucleic acids are subjected to PCR to detect the presence of nucleic acid unique to said Listeria.

32. A method for determining the quantity of Listeria in a sample, said method being capable of detecting one colony forming unit per 25 ml of sample, said method comprises:
   a) combining a sample to be tested for the presence of Listeria with a magnetic solid support having immobilized thereon first antibodies to said Listeria, to thereby capture cells of Listeria from said sample, said antibodies being attached to said solid support through an antibody linking compound such that the Fab portions of said antibodies extend outward from the surface of said solid support, said magnetic solid supporter being nonporous magnetic beads having a diameter of from 50 nm to 1 μm;
   b) exposing to a magnetic field said solid support having bound thereto said first antibodies and captured Listeria cells to thereby separate said magnetic solid support from said sample;
   c) culturing said magnetic solid support and captured bacteria cells on a solid medium to form colonies of said Listeria;
   d) contacting said colonies with a colony lift membrane whereby colony material from said colonies adheres to said membrane;
   e) contacting said membrane and said colony material adhered thereto with second antibodies specific for said Listeria, whereby said second antibodies bind to said colony material from said colonies of said Listeria;
   f) contacting said membrane with antibodies conjugated with a label and being specific for said second antibodies, whereby said labeled antibodies bind to said second antibodies bound to said colonies of said selected bacteria;
   g) treating said membrane to provide evidence of the presence on said membrane of said label and colonies of said Listeria; and
   h) determining the number of colonies on said membrane to provide a quantitative measure of the number of said Listeria in said sample.

33. The method according to claim 32, wherein said colony lift membrane is comprised of nitrocellulose or nylon.

34. The method according to claim 32, wherein after contacting with said colonies, said membrane is treated with a fixing agent to fix said colonies to said membrane.

35. The method according to claim 32, wherein said label is selected from the group consisting of fluorogenic, radioactive, chemiluminescent, bioluminescent, and enzyme substrate molecules.

36. The method according to claim 32, wherein said first antibodies are polyclonal antibodies to Listeria.

37. The method according to claim 36, wherein said second antibodies and labeled antibodies are monoclonal antibodies.

38. The method according to claim 32, wherein said labeled antibody is labeled with an enzymatic molecule, which when treated, produces a color change to provide visual evidence of the presence on said membrane of said label and colonies of said selected bacteria.

39. The method according to claim 38, wherein said enzymatic molecule is peroxidase, alkaline phosphatase, β-galactosidase, β-glucuronidase, α-glucosidase, β-glucosidase, α-mannosidase, galactose oxidase, glucose oxidase, or hexokinase.

40. The method according to claim 38, wherein said membrane is treated with a chromogenic substance for said enzymatic molecule.

41. A method for detecting the presence of bacteria in a sample which comprises:
   a) combining a sample to be tested for the presence of a selected bacteria with a magnetic solid support having immobilized thereon antibodies to said selected bacteria, to hereby capture cells of said selected bacteria from said sample, said magnetic solid support being non-porous magnetic beads having a diameter of from 50 nm to 1 μm;

b) exposing to a magnetic field said magnetic beads having bound thereto said antibodies and captured bacteria cells to thereby separate said magnetic solid support from said sample;

c) culturing the thus captured magnetic solid support and captured bacteria cells on a solid medium to form colonies of said selected bacteria;

d) contacting said colonies with a colony lift membrane whereby colony material adheres to said membrane; and e) treating said membrane to detect the presence on said membrane of material from said colonies of said selected bacteria.

42. The method according to claim 41, wherein said antibodies to said selected bacteria are bound to said magnetic solid support through an antibody linking compound.

43. The method according to claim 42, wherein said antibody linking compound is protein A.

44. The method according to any one of claims 41–43, wherein said membrane having colony material adhered thereto is contacted with second antibodies specific for said selected bacteria, whereby said second antibodies bind to said colony material from said colonies of said selected bacteria; said membrane is subsequently contacted with labeled antibodies specific for said second antibodies, and the presence of said label on said membrane is detected to thereby detect the presence of said selected bacteria in said sample.

45. The method according to any one of claims 41–43, wherein said membrane is contacted with labeled antibodies specific for said selected bacteria, whereby said labeled antibodies bind to said colony material from said selected bacteria, and the presence of said label on said membrane is detected to thereby detect the presence of said selected bacteria in said sample.

46. The method according to claim 45, wherein after said membrane with colony material adhered thereto is contacted with said labeled antibodies, the number of colonies having labeled detector antibodies bound thereto is counted to provide a quantitative measure of the number of said selected bacteria in said sample.

47. The method according to claim 46, wherein said label is selected from the group consisting of fluorogenic, radioactive, chemiluminescent, bioluminescent, and enzyme substrate molecules.

48. The method according to claim 41, wherein said lift membrane having colony material adhered thereto is combined with a lysis buffer to lyse bacteria and release nucleic acids from said selected bacteria, said released nucleic acids are combined with and hybridized to a nucleic acid probe specific for said selected bacteria, and formation of a hybrid molecule is detected.

49. The method according to claim 41, wherein said lift membrane having colony material adhered thereto is combined with a lysis buffer to lyse bacteria and release nucleic acids from said selected bacteria, and said released nucleic acids are subjected to PCR to detect the presence of nucleic acid unique to said selected bacteria.

50. A method for detecting the presence of bacteria in a sample, said method being capable of detecting one colony forming unit per 25 ml of sample, said method comprises:

a) combining a sample to be tested for the presence of a selected bacteria with a magnetic solid support having immobilized thereon first antibodies to said selected bacteria, to thereby capture cells of said selected bacteria from said sample, said antibodies being attached to said solid support through an antibody linking compound such that the Fab portions of said antibodies extend outward from the surface of said solid support, said magnetic solid support being nonporous magnetic beads having a diameter of from 50 nm to 1 µm;

b) exposing to a magnetic field said solid support having bound thereto said first antibodies and captured bacteria cells to thereby separate said magnetic solid support from said sample;

c) culturing said magnetic solid support and captured bacteria cells on a solid medium to form colonies of said selected bacteria;

d) contacting said colonies with a colony lift membrane whereby colony material from said colonies adheres to said membrane; and e) treating said membrane to detect the presence on said membrane of material from said colonies of said selected bacteria.

51. The method according to claim 50, wherein said antibody linking compound is protein A.

52. The method according to claim 50 or 51, wherein said membrane having colony material adhered thereto is contacted with second antibodies specific for said selected bacteria, whereby said second antibodies bind to said colony material from said colonies of said selected bacteria; said membrane is subsequently contacted with labeled antibodies specific for said second antibodies, and the presence of said label on said membrane is detected to thereby detect the presence of said selected bacteria in said sample.

53. The method according to claim 50 or 51, wherein said membrane is contacted with labeled antibodies specific for said selected bacteria, whereby said labeled antibodies bind to said colony material from said selected bacteria, and the presence of said label on said membrane is detected to thereby detect the presence of said selected bacteria in said sample.

54. The method according to claim 53, wherein after said membrane with colony material adhered thereto is contacted with said labeled antibodies, the number of colonies having labeled detector antibodies bound thereto is counted to provide a quantitative measure of the number of said selected bacteria in said sample.

55. The method according to claim 50, wherein said lift membrane having colony material adhered thereto is combined with a lysis buffer to lyse bacteria and release nucleic acids from said selected bacteria, said released nucleic acids are combined with and hybridized to a nucleic acid probe specific for said selected bacteria, and formation of a hybrid molecule is detected.

56. The method according to claim 50, wherein said lift membrane having colony material adhered thereto is combined with a lysis buffer to lyse bacteria and release nucleic acids from said selected bacteria, and said released nucleic acids are subjected to PCR to detect the presence of nucleic acid unique to said selected bacteria.

57. A method for determining the quantity of Listeria in a sample which comprises:

a) combining a sample to be tested for the presence of Listeria with a magnetic solid support having immobilized thereon antibodies to said Listeria, to thereby capture cells of said Listeria from said sample, said antibodies being attached to said solid support through an antibody linking compound such that the Fab portions of said antibodies extend outward from the surface of said solid support, said magnetic solid support being non-porous magnetic beads having a diameter of from 50 nm to 1 µm;

b) exposing to a magnetic field said magnetic beads having bound thereto said antibodies and captured Listeria cells to thereby separate said magnetic solid support from said sample;

c) culturing said magnetic solid support and captured Listeria cells on a solid medium to form colonies of said Listeria;

d) contacting said colonies with a colony lift membrane whereby some colony material adheres to said membrane; and e) treating said membrane to detect the presence on said membrane of material from said colonies of said Listeria and to provide a quantification of the amount of Listeria in said sample.

58. The method according to claim 57, wherein said antibody linking compound is protein A.

59. The method according to claim 57 or 58, wherein said membrane having colony material adhered thereto is contacted with second antibodies specific for said selected bacteria, whereby said second antibodies bind to said colony material from said colonies of said selected bacteria; said membrane is subsequently contacted with labeled antibodies specific for said second antibodies, and the presence of said label on said membrane is detected to thereby detect the presence of said selected bacteria in said sample.

60. The method according to claim 57 or 58, wherein said membrane is contacted with labeled antibodies specific for said Listeria, whereby said labeled antibodies bind to said colony material from said Listeria, and the presence of said label on said membrane is detected to thereby detect the presence of said Listeria in said sample.

61. The method according to claim 60, wherein after said membrane with colony material adhered thereto is contacted with said labeled antibodies, the number of colonies having labeled detector antibodies bound thereto is counted to provide a quantitative measure of the number of said Listeria in said sample.

62. The method according to claim 1, wherein said non-porous magnetic beads have a diameter of about 1 μm.

63. The method according to claim 9, wherein said non-porous magnetic beads have a diameter of about 1 μm.

64. The method according to claim 13, wherein said non-porous magnetic beads have a diameter of about 1 μm.

65. The method according to claim 24, wherein said non-porous magnetic beads have a diameter of about 1 μm.

66. The method according to claim 25, wherein said non-porous magnetic beads have a diameter of about 1 μm.

67. The method according to claim 28, wherein said non-porous magnetic beads have a diameter of about 1 μm.

68. The method according to claim 32, wherein said non-porous magnetic beads have a diameter of about 1 μm.

69. The method according to claim 37, wherein said non-porous magnetic beads have a diameter of about 1 μm.

70. The method according to claim 41, wherein said non-porous magnetic beads have a diameter of about 1 μm.

71. The method according to claim 43, wherein said non-porous magnetic beads have a diameter of about 1 μm.

72. The method according to claim 51, wherein said non-porous magnetic beads have a diameter of about 1 μm.

73. The method according to claim 53, wherein said non-porous magnetic beads have a diameter of about 1 μm.

74. The method according to claim 58, wherein said non-porous magnetic beads have a diameter of about 1 μm.

75. The method according to claim 60, wherein said non-porous magnetic beads have a diameter of about 1 μm.

* * * * *